(12) United States Patent
Bosley, Jr. et al.

(10) Patent No.: US 8,968,761 B2
(45) Date of Patent: Mar. 3, 2015

(54) PARTICULATE TISSUE GRAFT WITH COMPONENTS OF DIFFERING DENSITY AND METHODS OF MAKING AND USING THE SAME

(71) Applicants: Rodney W. Bosley, Jr., Chester Springs, PA (US); Clay Fette, Palm Beach Gardens, FL (US); Robert S. Tullius, Brookston, IN (US)

(72) Inventors: Rodney W. Bosley, Jr., Chester Springs, PA (US); Clay Fette, Palm Beach Gardens, FL (US); Robert S. Tullius, Brookston, IN (US)

(73) Assignee: ACell, Inc., Columbia, MD (US)

( * ) Notice: Subject to any disclaimer, the term of this patent is extended or adjusted under 35 U.S.C. 154(b) by 155 days.

(21) Appl. No.: 13/681,610

(22) Filed: Nov. 20, 2012

(65) Prior Publication Data
US 2013/0115255 A1    May 9, 2013

Related U.S. Application Data

(62) Division of application No. 12/507,311, filed on Jul. 22, 2009, now Pat. No. 8,652,500.

(51) Int. Cl.
| | | |
|---|---|---|
| A61F 13/00 | (2006.01) | |
| A61F 2/00 | (2006.01) | |
| A61K 35/12 | (2006.01) | |
| A61L 27/26 | (2006.01) | |
| A61L 27/36 | (2006.01) | |
| A61L 27/58 | (2006.01) | |

(52) U.S. Cl.
CPC ............. *A61K 35/12* (2013.01); *A61L 27/26* (2013.01); *A61L 27/3633* (2013.01); *A61L 27/58* (2013.01)
USPC .......................... 424/422; 424/572; 424/426

(58) Field of Classification Search
None
See application file for complete search history.

(56) References Cited

U.S. PATENT DOCUMENTS

| | | | |
|---|---|---|---|
| 3,562,820 A | 2/1971 | Braun | |
| 4,439,521 A | 3/1984 | Archer et al. | |
| 4,703,108 A | 10/1987 | Silver et al. | |
| 4,776,653 A | 10/1988 | Klement et al. | |
| 4,780,450 A | 10/1988 | Sauk et al. | |
| 4,801,299 A | 1/1989 | Brendel et al. | |
| 4,829,000 A | 5/1989 | Kleinman et al. | |
| 4,902,508 A | 2/1990 | Badylak et al. | |
| 4,956,178 A | 9/1990 | Badylak et al. | |
| 5,275,826 A * | 1/1994 | Badylak et al. ............... 424/551 |
| 5,281,422 A | 1/1994 | Badylak et al. | |
| 5,336,616 A | 8/1994 | Livesey et al. | |
| 5,352,463 A | 10/1994 | Badylak et al. | |
| 5,372,821 A | 12/1994 | Badylak et al. | |
| 5,425,769 A * | 6/1995 | Snyders, Jr. ................ 623/23.61 |
| 5,445,833 A | 8/1995 | Badylak et al. | |
| 5,516,533 A | 5/1996 | Badylak et al. | |
| 5,554,389 A | 9/1996 | Badylak et al. | |
| 5,573,784 A | 11/1996 | Badylak et al. | |
| 5,618,312 A | 4/1997 | Yui et al. | |
| 5,641,518 A | 6/1997 | Badylak | |
| 5,695,998 A | 12/1997 | Badylak et al. | |
| 5,711,969 A | 1/1998 | Patel et al. | |
| 5,753,267 A | 5/1998 | Badylak et al. | |
| 5,755,791 A | 5/1998 | Whitson et al. | |
| 5,762,966 A | 6/1998 | Knapp, Jr. et al. | |
| 5,866,414 A | 2/1999 | Badylak et al. | |
| 5,866,415 A | 2/1999 | Villeneuve et al. | |
| 5,869,041 A | 2/1999 | Vandenburgh | |
| 5,885,619 A | 3/1999 | Patel et al. | |
| 5,899,936 A | 5/1999 | Goldstein | |
| 5,916,266 A | 6/1999 | Yui et al. | |
| 6,051,750 A | 4/2000 | Bell | |
| 6,087,157 A | 7/2000 | Badylak et al. | |
| 6,096,347 A | 8/2000 | Geddes et al. | |
| 6,126,686 A | 10/2000 | Badylak et al. | |
| 6,171,344 B1 | 1/2001 | Atala | |
| 6,206,931 B1 | 3/2001 | Cook et al. | |
| 6,322,593 B1 | 11/2001 | Pathak et al. | |
| 6,376,244 B1 | 4/2002 | Atala | |
| 6,432,712 B1 | 8/2002 | Wolfinbarger, Jr. | |
| 6,454,804 B1 | 9/2002 | Ferree | |
| 6,455,311 B1 | 9/2002 | Vacanti | |
| 6,479,064 B1 | 11/2002 | Atala | |
| 6,485,723 B1 | 11/2002 | Badylak et al. | |
| 6,485,969 B1 | 11/2002 | Asem et al. | |
| 6,572,650 B1 | 6/2003 | Abraham et al. | |
| 6,576,265 B1 | 6/2003 | Spievack | |
| 6,579,538 B1 | 6/2003 | Spievack | |
| 6,613,348 B1 | 9/2003 | Jain | |
| 6,783,776 B2 | 8/2004 | Spievack | |
| 6,827,966 B2 | 12/2004 | Qiu et al. | |
| 6,849,273 B2 | 2/2005 | Spievack | |
| 6,852,339 B2 | 2/2005 | Spievack | |

(Continued)

FOREIGN PATENT DOCUMENTS

| | | |
|---|---|---|
| DE | 19828726 | 1/1999 |
| EP | 0747067 | 12/1996 |

(Continued)

OTHER PUBLICATIONS

Freytes et al. "Biaxial strength of multilaminated extracellular matrix scaffolds", Biomaterials, 25, 2004, pp. 2353-2361.*

(Continued)

*Primary Examiner* — Kortney L Klinkel
*Assistant Examiner* — Melissa Javier
(74) *Attorney, Agent, or Firm* — Burns & Levinson LLP

(57) ABSTRACT

Disclosed are tissue graft compositions made of particles having different densities, methods of making these compositions, and methods of using these compositions for promoting tissue restoration in a patient.

17 Claims, 9 Drawing Sheets

(56) References Cited

U.S. PATENT DOCUMENTS

| | | | |
|---|---|---|---|
| 6,861,074 B2 | 3/2005 | Spievack | |
| 6,869,619 B2 | 3/2005 | Spievack | |
| 6,887,495 B2 | 5/2005 | Spievack | |
| 6,890,562 B2 | 5/2005 | Spievack | |
| 6,890,563 B2 | 5/2005 | Spievack | |
| 6,890,564 B2 | 5/2005 | Spievack | |
| 6,893,666 B2 | 5/2005 | Spievack | |
| 2002/0115208 A1 | 8/2002 | Mitchell et al. | |
| 2002/0172705 A1 | 11/2002 | Murphy et al. | |
| 2003/0039742 A1 | 2/2003 | Qiu et al. | |
| 2003/0054022 A1 | 3/2003 | Spievack | |
| 2003/0059404 A1 | 3/2003 | Spievack | |
| 2003/0059405 A1 | 3/2003 | Spievack | |
| 2003/0059406 A1 | 3/2003 | Spievack | |
| 2003/0059407 A1 | 3/2003 | Spievack | |
| 2003/0059409 A1 | 3/2003 | Spievack | |
| 2003/0059410 A1 | 3/2003 | Spievack | |
| 2003/0059411 A1 | 3/2003 | Spievack | |
| 2003/0064111 A1 | 4/2003 | Spievack | |
| 2003/0064112 A1 | 4/2003 | Spievack | |
| 2003/0133916 A1 | 7/2003 | Spievack | |
| 2003/0211130 A1 | 11/2003 | Sanders et al. | |
| 2004/0043006 A1* | 3/2004 | Badylak et al. | 424/93.7 |
| 2004/0175366 A1 | 9/2004 | Badylak | |
| 2005/0106207 A1 | 5/2005 | Qiu et al. | |
| 2005/0175659 A1 | 8/2005 | Macomber et al. | |
| 2005/0283256 A1 | 12/2005 | Sommerich et al. | |
| 2007/0254041 A1 | 11/2007 | Drapeau et al. | |
| 2007/0254042 A1 | 11/2007 | Drapeau et al. | |
| 2011/0020418 A1 | 1/2011 | Bosley | |

FOREIGN PATENT DOCUMENTS

| | | |
|---|---|---|
| EP | 0773033 A1 | 5/1997 |
| WO | 9300441 | 1/1993 |
| WO | 9524873 | 9/1995 |
| WO | 9717038 | 5/1997 |
| WO | 9822158 | 5/1998 |
| WO | WO9822154 | 5/1998 |
| WO | 9825545 | 6/1998 |
| WO | 9825546 | 6/1998 |
| WO | 9825637 | 6/1998 |
| WO | 9846165 | 10/1998 |
| WO | 0015765 | 3/2000 |
| WO | 0145765 | 6/2001 |
| WO | 0214480 | 2/2002 |
| WO | 03002168 | 1/2003 |
| WO | 03043674 | 5/2003 |
| WO | 2005094694 | 10/2005 |
| WO | 2008001228 | 1/2008 |
| WO | 2008012828 | 1/2008 |
| WO | WO2008012828 | 1/2008 |
| WO | 2009076391 | 6/2009 |

OTHER PUBLICATIONS

Freytes et al., "Biaxial strength of multilaminated extracellular matrix scaffolds", Biomaterials, 25, 2004, 2353-2361.

Gilbert et al., "Production and characterization of ECM powder: implication for tissue engineering applications", Biomaterials, 26, 2005, pp. 1431-1435.

Podrazky et al., "Densities of collagen dehydrated by some organic solvents", Cellular and Molecular Life Sciences, 22(12), 1966, 792.

Calcium Carbonate by Sigma-Aldrich, accessed Aug. 3, 2011, http://www.sigmaaldrich.com/catalog/ProductDetail.do?D7=0&N5=SEARCH_CONCAT_PNO%7CBRAND_KEY&N4=310034%7CALDRICH&N25=0$QS=ON&F=SPEC.

International Search Report and Written Opinion of the ISA issued in a concurrently filed PCT application PCT/US2010/042701, mailed on Feb. 16, 2001; 11 pages.

Badylak et al., "Small intestinal submucosa: a substrate for in vitro cell growth," J. Biomat. Science 9:863-878 (1998).

Badylak et al., "Endothelial cell adherence to small intestinal submucosa: an acellular bioscaffold," 20:2257-2263 (1999).

Badylak et al., "Marrow-derived cells populate scaffolds composed of xenogeneic extracellular matris," Experimental Hematology 29:1310-1318 (2001).

Badylak et al., "Resorbable Bioscaffold for Esophageal Repair in a Dog Model," Journal of Pediatric Surgery 35:7:1097-1103 (2000).

Dahms et al., "Bladder Acellular Matrix Graft in Rats: Its Neurophysiologic Properties and mRNA Expression of Growth Factors TGF-a and TGF-b," Neurology and Urodynamics 17:37-54 (1998).

Dahms et al., "Composition and biomechanical properties of the bladder acellular matrix graft: comparative analysis in rat, pig and human," British Journal of Urology 82:411-419 (1998).

Dahms et al., "Free Ureteral Replacement in Rats: Regeneration of Ureteral Wall Components in the Acellular Matrix Graft," Urology 50(5) 818-825 (1997).

Hadlock et al., "A New Artificial Nerve Graft Containing Rolled Schwann Cell Monolayers," Microsurgery 21:96-101 (2001).

Lakey et al., "Improved Islet Survival and In Vitro Function Using Small Intestinal Submucosa," Transplantation Proceedings 30:383 (1998).

Lindberg et al., "Porcine small intestinal submucosa (SIS): a bioscaffold supporting in vitro primary human epidermal cell differentiation and synthesis of basement membrane proteins," Burns 27:254-266 (2001).

Mouri et al., "Defenestration of the Sinusoidal Endothelial Cell in a Rat Model of Cirrhosis," Hepatology 17:5:891-897 (1993).

Pariente et al., "In Vitro Biocompatibility Assessment of Naturally Derived and Synthetic Biomaterials using Normal Human Urothelial Cells," J. Biomed. Mater. Res. 55:33-39 (2001).

Pariente et al., "In Vitro Biocompatibility Evaluation of Naturally Derived and Synthetic Biomaterials using Normal Human Bladder Smooth Muscle Cells," The Journal of Urology 167:1867-1871 (2002).

Peel et al., "Formation of a SIS-cartilage composite graft in vitro and its use in the repair of articular cartilage defects," Tissue Eng. 4:143-155 (1998).

Piechota et al., "Bladder acellular matrix graft: in vivo functional properties of the regenerated rat bladder," Urol. Res. 27:206-213 (1999).

Piechota et al., "Functional rat bladder regeneration through xenotransplantation of the bladder acellular matrix graft," British Journal of Urology 81:548-559 (1998).

Picchota et al., "In Vitro Functional Properties of the Rat Bladder Regenerated by the Bladder Acellular Matrix Graft," Journal of Urology 159:1717-1724 (1998).

Probst et al., "Homologous bladder augmentation in dog with the bladder acellular matrix graft," BJU International 85:362-371 (2000).

Rosenthal et al., "The Mucosal Invasion Model," Arch Otolaryngol Head Neck Surgery 127:1467-1470 (2001).

Voytik-Harbin et al., "Small intestinal submucosa: A tissue-derived extracellular matrix that promotes tissue-specific growth and differentiation of cells in vitro," Tissue Eng. 4:157-174 (1998).

Voytik-Harbin et al., "Three-dimensional imaging of extracellular matrix and extracellular matrix-cell interactions," Methods Cell Biol. 63:583-597 (2001).

Voytik-Harbin, "Three-dimensional extracellular matrix substrates for cell culture," Methods Cell Biol. 63:561-581 (2001).

Yoo et al., "Bladder Augmentation using Allogenic Bladder Submucosa Seeded with Cells," Urology 51(2):221-225 (1998).

Zhange et al., "Coculture of Bladder Urothelial and Smooth Muscle Cells on Small Intestine Submucosa: Potential Applications for Tissue Engineering Technology," The Journal of Urology 164:928-935 (2000).

English translation of an Office action issued in a counterpart Japanese patent application No. 2012-521747on Jun. 10, 2014 (4 pages).

\* cited by examiner

PARTICULATE TISSUE GRAFT WITH COMPONENTS OF DIFFERING DENSITY AND METHODS OF MAKING AND USING THE SAME

CROSS REFERENCE TO RELATED APPLICATION

This application is a divisional application claiming priority to and benefit of co-pending U.S. patent application Ser. No. 12/507,311, filed on Jul. 22, 2009, the entire contents of which are incorporated herein by reference.

TECHNICAL FIELD OF THE INVENTION

The present invention is related to particulate tissue graft compositions, methods of making them, and methods of using them to repair or restore tissues in a patient.

BACKGROUND

Tissue graft compositions made of devitalized native tissues have been widely used to repair or restore damaged, deformed, or missing tissues in patients. Typically these compositions are made from the extracellular matrix of tissues, for example, the submucosa of the intestine (SIS), or urinary bladder (UBS), and the epithelial basement membrane of for example, the urinary bladder (UBM). Collectively these compositions are termed extracellular matrices or ECMs. SN, UBS, and UBM are further described in U.S. Pat. Nos. 6,576,265, 6,579,538, 5,573,784, 5,554,389, 4,956,178, and 4,902,508, each of which are incorporated by reference herein.

Briefly, SIS and UBS are made from gastrointestinal tissue and urinary bladder, respectively by delaminating the submucosa from all other layers of the tissue source and retaining the submucosa to form a tissue graft composition. UBM is made by delaminating the epithelial basement membrane and, optionally, delaminating one or more of the deeper layers from the epithelial cells of the urinary bladder and retaining at least the epithelial basement membrane to form a tissue graft composition. Other tissues including, but not limited to skin and tissues of the gastrointestinal tract, e.g., esophagus, stomach, and intestine, may also be used to make an ECM including epithelial basement membrane by delaminating the epithelial basement membrane from the epithelial cells and, optionally; one or more of the deeper layers of the tissue source. Still other native ECMs may be made from connective tissues such as aponeurosis, tendon, ligament, smooth and skeletal muscle, and treatment-site specific ECMs, ECMs are used to restore, for example, epithelial tissues. Restoration of epithelial tissues requires restoration of the epithelium and the connective tissue elements underlying the epithelial tissue. Epithelial restoration occurs rapidly when epithelial basement membrane is present. However, restoration of the connective tissue elements is slower than epithelial tissue restoration, prolonging the complete restoration of damaged epithelial tissues.

Each of the ECMs, such as UBS, UBM, and SIS, known in the prior art, are resorbed at the site of implantation in a patient. For example, a single sheet of urinary bladder matrix (UBM) may resorb, for example, within a week when implanted in a topical wound. FIGS. 1A-C depict the rapid resorption profile of a prior art ECM material 12 implanted at a tissue site 10 in a patient. FIG. 1A shows the sheet of ECM 12 on day 0 of implantation. As shown, the ECM 12 fills the entire tissue site 10. At day X after implantation, FIG. 1B shows that the ECM 12 has been partially resorbed at the tissue site 10 as shown by the reduced surface area of the ECM 12 as compared to the surface area of the ECM 12 in FIG. 1A. At day Y after implantation, FIG. 1C shows that the ECM 12 has been completely resorbed by the tissue site 10 as no ECM 12 remains.

SUMMARY OF THE INVENTION

According to the invention, a preferred devitalized matrix for mammalian tissue repair or regeneration comprises at least a portion of a mammalian epithelial basement membrane, preferably the entire epithelial basement membrane, and the tunica propria that is immediately subjacent to the basement membrane. Devitalized matrices of the invention restore or replace diseased, defective, or missing tissue when placed in contact with host tissue. In a preferred embodiment, the invention comprises a devitalized matrix that is custom-shaped to conform to the diseased or defective tissue. In a particular embodiment, the matrix comprises a sheet of matrix derived from the urinary bladder, the intestine, or any other mammalian epithelial tissue. In another embodiment, the matrix is injectable by means of being transformed into a fine particulate, emulsion, gel or extract. A matrix of the invention may act as a carrier for a pharmaceutical agent. A preferred application of the matrix of the invention is the repair or restoration of cardiac tissue. In particular, a matrix or composition of the invention is useful to restore or replace at least a portion of a cardiac valve, the interatrial septum, the interventricular septum, or the myocardium. For the purposes of this invention, matrix and composition are interchangeable terms.

In one embodiment, the invention features a devitalized composition comprising epithelial basement membrane and tunica propria immediately subjacent to the basement membrane. The epithelial basement membrane and tunica propria immediately subjacent to the basement membrane are delaminated from cells of a mammalian epithelium and abluminal portions of the tunica propria. Mammalian epithelial tissue used in this aspect of the invention is preferably derived from urinary bladder, intestine, or any other mammalian epithelial tissue. Further embodiments feature a composition shaped to conform to a diseased or defective cardiac valve such as at least a portion of a pulmonic valve, aortic valve, right or left atrioventricular valve, or the myocardium.

In still another embodiment, the invention features a composition comprising epithelial basement membrane, tunica propria, and submucosa. The epithelial basement membrane and tunica propria are delaminated from the cells of an epithelium and from the tunica muscularis of a mammalian epithelial tissue.

In yet another embodiment, the invention features a composition comprising epithelial basement membrane, tunica propria, and smooth muscle cells of the tunica muscularis, all delaminated from epithelial cells of a mammalian epithelium.

The composition, according to the invention, is not limited to merely the embodiments enclosed. Rather, the composition, according to the invention, comprises one or more layers of an epithelial tissue in combination with at least a portion, preferably the entire, intact epithelial basement membrane.

A preferred method of the invention comprises the step of contacting a host tissue with a devitalized matrix derived from a mammal. The devitalized matrix comprises at least a portion of an epithelial basement membrane and tunica propria immediately subjacent to the basement membrane. In preferred embodiments, methods of the invention comprise inducing endogenous epithelial repair using tissue regenerative compositions of the invention.

The invention disclosed herein has identified and solved the problem of prior art ECM implants that are rapidly resorbed and are subsequently no longer available to influence restoration and repair of damaged or missing epithelial tissues and the underlying connective tissue elements. While the rapid initial resorption of prior art ECMs is beneficial in providing an initial restoration response to the tissue site in need of restoration or repair, the invention described herein is advantageous because it provides, at the site in need of restoration or repair, an ECM composition that takes longer to resorb than the prior art ECMs which prolongs the ECMs influence on the repair process at the site of tissue injury. Accordingly, the invention disclosed herein is directed to an ECM composition having at least one component that resorbs quickly to provide a rapid initial repair response, but also having at least one additional component that resorbs more slowly in order to prolong the influence of the ECM composition combination on the restoration process at the site of tissue injury.

According to one aspect, the invention relates to compositions of bioresorbable particles useful for tissue repair or restoration and methods of using these compositions. The compositions include bioresorbable particles of differing density which resorb at different rates, thereby providing the ability to adjust the length of time provided by the particles to effect repair as compared to compositions having materials of a single density.

According to one aspect, the invention includes tissue graft compositions of bioresorbable particles. In one embodiment of the invention, a mixture of bioresorbable particulate matter comprises a first plurality of bioresorbable particles having a first density and a first rate of resorption on implantation at a tissue site in the patient and a second plurality of particles having a second density and a second rate of resorption on implantation at the tissue site in the patient. The second density is at least 150% of the first density. The second rate of resorption is in the range of about 1 to about 10 times the first rate of resorption. The first plurality and second plurality of bioresorbable particles promote tissue restoration and repair when implanted at a tissue site in a mammalian patient.

In one embodiment, the first plurality of particles comprises a first bioresorbable material and the second plurality of particles comprises a second bioresorbable material, whereas in another embodiment the first plurality of particles and the second plurality of particles comprise the same bioresorbable material. The first or second bioresorbable material may be selected from, for example, extracellular matrix, collagen, a bioresorbable polymer, or hyaluronic acid. The particles may be in powder form, dispersed in a liquid or gel medium, or compressed into a sheet form. The size of the particles may range from 1 µm to 1000 µm. In a further embodiment, the particles may include one or more bioactive factors, pharmaceutical agents, or DNA vectors. The first plurality of particles and the second plurality of particles may be present in a ratio of 1:1. The second density may be in the range from 150% to 500% of the first density.

in yet another embodiment, the tissue graft composition includes a third plurality of particles having a third density that is more dense than the first and second densities and a third rate of resorption that is slower than the first and second rates of resorption on implantation at the tissue site in a patient.

According to another aspect, the invention includes methods for preparing mixtures of bioresorbable particles having different densities. For example, in one embodiment, a method for preparing a mixture of bioresorbable particulate matter having differing densities comprises providing a first sheet of bioresorbable material having a first density and a first rate of bioresorption and milling the sheet into a first plurality of particles. A second sheet of a bioresorbable material having a second density and a second rate of bioresorption is milled into a second plurality of particles. A predetermined quantity of the first plurality of particles is mixed with a predetermined quantity of the second plurality of particles, wherein the density of the second plurality of particles is at least 150% of the density of the first plurality of particles and wherein the first rate of resorption is at least 1.5 times that of the second rate of resorption. The first plurality of particles and the second plurality of particles are capable of promoting tissue restoration and repair when implanted at a tissue site in a mammalian patient.

According to another embodiment of the invention, the second sheet may be compressed or laminated prior to milling to increase its density relative to the first sheet. In an alternative embodiment, the first sheet may be lyophilized prior to milling to reduce its density relative to the second sheet.

According to another embodiment of the invention, the sheet may be milled into particles by comminuting, grinding, chopping, blending, pulverizing, or mincing. In a further embodiment, the first or second sheet is dried, hydrated or frozen prior to milling.

According to another embodiment of the invention, the bioresorbable material comprises extracellular matrix, hyaluronic acid or a bioresorbable polymer. The hyaluronic acid or bioresorbable polymer may be chemically synthesized or precipitated to form sheets of a first density and sheets of a second density prior to milling.

According to yet another embodiment, the first sheet and the second sheet may comprise the same bioresorbable material. For example, in one embodiment the first and second sheet are extracellular matrix. In another embodiment, the first and second sheet are aponeurosis. In an alternative embodiment, the first sheet and the second sheet comprise different bioresorbable materials. For example, in one embodiment the first sheet comprises extracellular matrix and the second sheet comprises hyaluronic acid. In another embodiment, the first or second sheet further comprises one or more pharmaceutical agents, DNA vectors, or bioactive factors such as a growth factor.

In yet another embodiment, the second density of the second sheet is 150%-500% of the first density.

In yet another embodiment, the particles of a first density and the particles of a second density prepared by the method are compressed into a sheet form.

In another embodiment of the invention, a method for preparing a mixture of bioresorbable particulate matter having differing densities comprises providing a sheet of bioresorbable material of a first density and compressing a portion of the sheet such that the portion comprises a second density that is at least 150% or as much as 150%-500% of the first density. The sheet is milled into a plurality of particles. In a further embodiment, the bioresorbable material is ECM.

In another aspect, the invention provides methods of promoting tissue repair and restoration at an anatomical site in a patient. For example, according to one embodiment, a method of modulating the rate of tissue repair at an anatomical site in a patient in need of repair or restoration comprises administering to a patient at the site a mixture comprising a first plurality of bioresorbable particles having a first density and a second plurality of bioresorbable particles having a second density at least 150% of the first density; wherein the second plurality of bioresorbable particles are resorbed by the patient's tissue at a slower rate than the absorption of the first plurality of bioresorbable particles, thereby prolonging the therapeutic effect of the second plurality of particles at the site. The first plurality and second plurality of bioresorbable particles promote tissue restoration and repair when implanted at the anatomical site in a mammalian patient. In a further embodiment, the mixture comprises a third plurality of particles having a third density.

In a further embodiment, the method also includes the steps of preparing the mixture of bioresorbable particles which include the steps of (a) determining the optimal rate of absorption of a resorbable composition for repair or restoration of the site in the patient, (b) selecting the first plurality of bioresorbable particles to have a first density and a first rate of absorption based on step (a) on implantation at a site in the patient, and (c) selecting the second plurality of bioresorbable particles to have a second density more dense than the density of the first plurality of particles and having a second rate of absorption based on step (a) and step (b) slower than the rate of absorption of the first plurality of bioresorbable particles on implantation at the site in the patient.

According to one embodiment of the method, the bioresorbable particles are extracellular matrix, collagen, a bioresorbable polymer, or hyaluronic acid. The bioresorbable particles may be delivered to the site in the patient in powder form or in a liquid or gel medium. The bioresorbable particles may also be injected at the site in the patient. The bioresorbable particles may contain one or more bioactive factors, DNA vectors, or pharmaceutical agents.

In another embodiment of the method, a mixture of bioresorbable particles is administered to the patient via coating the mixture on a medical device prior to implantation of the medical device at the site in the patient, whereas in an alternative embodiment, the mixture is administered topically to the site. In a further embodiment, the mixture is administered to the patient as a component of a bone substitute material.

According to a further embodiment of the method, the site in need of repair or restoration in the patient is a tendon, ligament, bone, kidney, liver, spleen, lymph node, urinary bladder, ureter, uterus, blood vessel, skin, breast, heart, or a body cavity. In one embodiment, the patient is a human.

According to another aspect, the invention includes an implant for implanting in a patient comprising particles of extracellular matrix of a first density and having a first rate of resorption in a patient and particles of extracellular matrix of a second density and having a second rate of resorption in a patient, where said particles are compressed to form a three-dimensional object. The particles of the first density and the particles of the second density promote tissue restoration and repair when implanted at a tissue site in a human patient.

According to one embodiment, the extracellular matrix is UBS, SIS, or UBM. In another embodiment, the particles of a first density are UBS and the particles of a second density are UBM. In another embodiment of the implant, the particles of the first density are more dense than the particles of the second density and the particles of the first density form a core of the implant and the particles of the second density form the exterior surface of the implant.

In another aspect, the invention includes implanting the implant in a patient in need of tissue repair. In a further embodiment, the implant site may be a tendon, ligament, bone, kidney, liver, spleen, lymph node, urinary bladder, ureter, uterus, blood vessel, skin, breast, heart, or a body cavity.

In yet another aspect, the invention includes a method of preparing a mixture of particles of extracellular matrix which comprises preparing a plurality of particles of extracellular matrix having the same density, coating a first portion of the plurality of particles with a coating having a first density and a first rate of absorption in a patient, coating a second portion of the plurality of particles with a coating having a second density and a second rate of absorption in a patient, and mixing the first portion of the plurality of particles with the second portion of the plurality of particles. The plurality of particles promote tissue restoration and repair when implanted at a tissue site in a mammalian patient. In one embodiment, the particles of extracellular matrix include urinary basement membrane (UBM), the coating of the first portion of the plurality of particles having a first density is UBM, and the coating of the second portion of the plurality of particles having a second density is small intestinal submucosa (SIS).

In yet another aspect, the invention is a composition of extracellular matrix. The composition comprises a first sheet of extracellular matrix, a second sheet of extracellular matrix, and a first plurality of extracellular matrix particles having a first density and a second plurality of extracellular matrix particles having a second density at least 150% of the first density, wherein the first plurality of particles and the second plurality of particles are contained between the first sheet and the second sheet of extracellular matrix. The first plurality and second plurality of extracellular matrix particles promote tissue restoration and repair when implanted at a tissue site in a mammalian patient.

In a further embodiment, the composition includes a further plurality of extracellular matrix particles having a density of either the first density, the second density, or a third density, wherein the further plurality of particles are positioned between the surface of either the first sheet or second sheet of extracellular matrix and a third sheet of extracellular matrix.

BRIEF DESCRIPTION OF THE FIGURES

FIG. 1A depicts the ECM on Day 0 at implantation. FIG. 1B depicts the ECM on Day X after implantation where the ECM has been partially resorbed by the patient tissue. FIG. 1C depicts the ECM on Day Y after implantation where the ECM has been fully resorbed by the patient tissue.

FIG. 2A depicts the particles on Day 0 at implantation. FIG. 2B depicts the particles on Day X after implantation where the lower density particles have been partially resorbed by the patient tissue, as evidenced by their decrease in size. FIG. 2C depicts the particles on Day Y after implantation where the lower density particles have been fully resorbed by the patient tissue, and the higher density particles have not yet been fully resorbed by the patient tissue.

DETAILED DESCRIPTION OF THE INVENTION

Figure 1A:
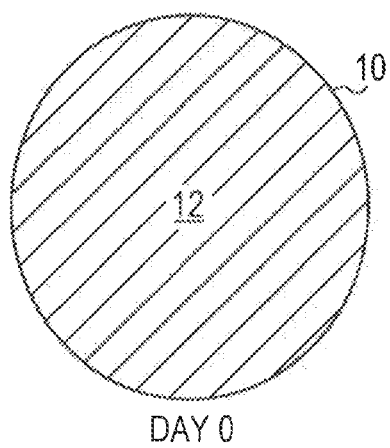
FIGS. 1A-C depict the bioresorption of a prior art ECM such as UBM, UBS, SIS in a mammalian patient tissue.

Extracellular matrix materials (ECMs) have been used to promote repair and restoration of damaged, deformed, injured, and even missing body tissues in mammals, such as humans. For example, ECMs such as SIS or UBM are implanted at a treatment site to promote repair and restoration of epithelial tissues and connective tissues, including connective tissue layers associated with epithelial tissues. Tissue sites in need of repair or restoration include, but are not limited to tendons, ligaments, breast, bone, kidney, liver, spleen, lymph nodes, urinary bladder, ureter, uterus, blood vessels, intestine, stomach, skin, heart, or a body cavity. "Restore," "restored," "restoring," or "restoration" means that tissue function and structure is substantially returned to its original condition by the patient's endogenous tissue repair mechanisms in combination with the tissue graft composition.

ECMs such as SIS, UBS, and UBM are rapidly resorbed by host tissues in which the ECM has been implanted. Once the material has been resorbed by the host, the ECM no longer has an influence over tissue restoration and repair at the site of implantation. As ECMs are resorbed, they release bioactive components such as growth factors and other bioactive components naturally present in the native ECM that influence tissue restoration and repair at the site of implantation of the ECM. Once the ECM has been fully resorbed, these growth factors and bioactive components are no longer released by the ECM at the implantation site to influence tissue repair and restoration, in order to moderate the appearance of these factors and components contributed by ECMs during repair of tissues, disclosed herein are compositions of ECM particles that have resorption times that vary from the rapid resorption times of known native ECMs.

In one aspect, the invention relates to tissue graft compositions of ECM particles where the particles vary in density. "Density" as used herein refers to mass per unit volume of the particle. According to one embodiment of the invention, ECMs are manipulated to alter their densities and are then particularized. The particles, when implanted in a patient, resorb at rates related to their densities, with lower density particles being resorbed by the patient at a faster rate than more dense particles. Lower density particles resorb more quickly than higher density particles, releasing growth factors and other bioactive components quickly, thereby modulating an initial repair response at the tissue site. In contrast, higher density particles resorb slowly, releasing growth factors and other bioactive components more slowly, thereby maintaining the repair response at the site of implantation beyond the initial repair response influenced by the growth factors and bioactive components released by the lower density particles.

According to the invention, having both lower and higher density particles as opposed to just higher density particles alone permits the released growth factors and other bioactive components provided by the lower density particles to modulate an initial rapid repair response at the tissue site due to the rapid resorption of the low density particles. Ideally, such a rapid repair response cannot be provided by the higher density particles alone because their resorption is slower and therefore, the release of bioactive components from the material that encourages tissue repair and restoration is also slower.

Traditional ECMs have a rapid resorption time such that the ECMs may be fully resorbed at the tissue implantation site before the tissue site is completely repaired. Increased density ECM particles or aggregates of ECM particles of varying densities prepared according to the invention have prolonged resorption times and can therefore have an extended influence over tissue repair and restoration at the site of the injury as compared to using traditional ECMs. In other words, tissue graft compositions according to the invention allow the tissue site to repair completely or close to completely before the tissue graft composition is bioresorbed at the tissue site. According to the invention, compositions of ECM particles provide a specific bioresorption profile tailored to the restoration needs of a specific tissue site in a patient.

The invention as described herein has the advantage of reducing the amount of space required to accommodate an ECM tissue graft construct at an implantation site in a patient. For example, by increasing the density of a tissue graft construct according to the invention, more ECM material can be included in a smaller volume. In addition, by increasing the density, the ECM material according to the invention takes longer to be resorbed at the implantation site in comparison to thicker, less dense ECM materials in the patient, thereby exerting a prolonged influence on tissue repair and restoration at the implantation site in the patient.

According to the invention, the rate of resorption of compositions can be measured based on the number of days required for a certain volume of ECM to be resorbed by host tissue at the site of implantation. For example, a composition according to the invention, in one embodiment, includes a lower density particle having a volume of 100 $\mu M^2$ and a density of X that takes 15 days to be resorbed and a higher density particle having a volume of 100 $\mu M^2$ and having a density of 2x that takes 45 days to be resorbed. According to the invention, there is not necessarily a direct linear relationship between density and resorption time. As shown by this example, a particle that is twice the density of a first less dense particle may take longer than twice the resorption time of the first less dense particle to be resorbed.

Figure 2A:
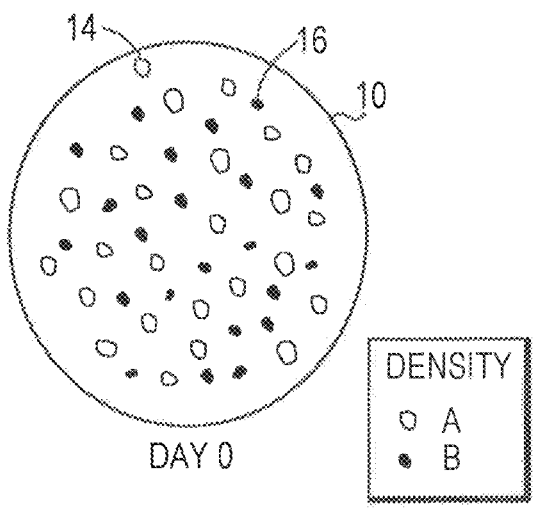
FIGS. 2A-C depict the bioresorption of an exemplary particulate tissue graft made up of two types of particles of different density according to one embodiment of the invention. The open circles (o) represent a lower density particle and the solid circles (•) represent a higher density particle.
Figure 1B:
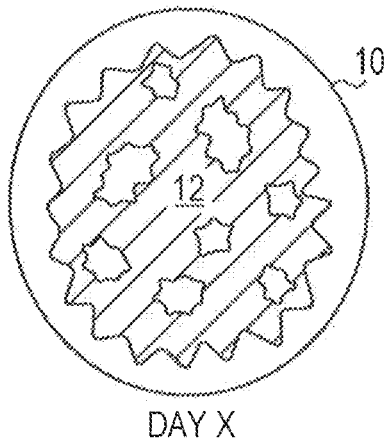
Figure 2B:
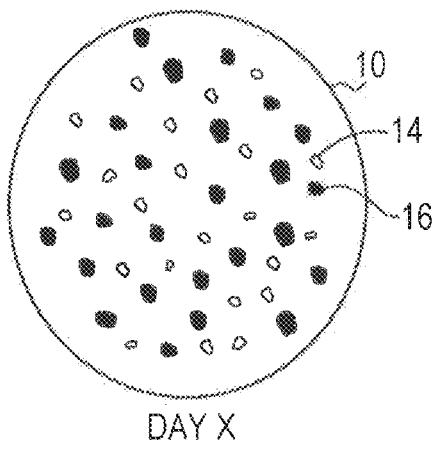
Figure 1C:
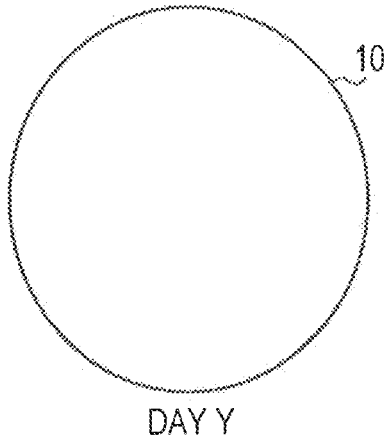
Figure 2C:
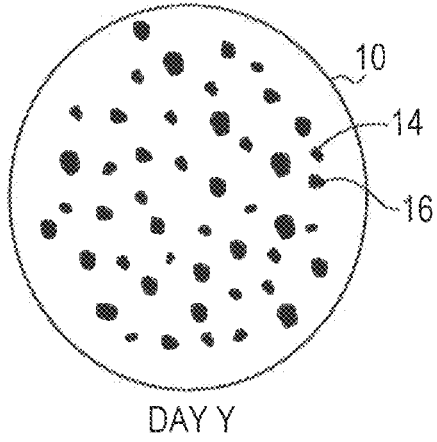

As previously mentioned, ECMs known in the art have a rapid bioresorption rate when implanted at a tissue site in a patient. In contrast to the rapid bioresorption profile demonstrated by known ECMs, compositions according to the invention have varied bioresorption times based on the density of particles in the tissue graft composition. For example, FIGS. 2A-C demonstrate the varied bioresorption profile of a tissue graft composition of particles of differing density according to the invention. FIG. 2A shows ECM particles 16 (of a higher density than the ECM shown in FIGS. 1A-C) and ECM particles 14 (of comparable density to the ECM shown in FIGS. 1A-C) on day 0, the day of implantation at the tissue site. At day X after implantation, as shown in FIG. 2B, the low density particles 14 have been partially resorbed as indicated by their reduced size. The more dense particles 16 have also not yet been fully resorbed. By day Y after implantation, as shown in FIG. 2C, the lower density particles 14 have been fully resorbed, while the more dense particles 16 have not, permitting the more dense particles to continue to promote tissue repair and restoration at the tissue site 10.

In one embodiment of the invention, a tissue graft composition of particles includes particles of a first density and particles of a second, different density. In a further embodiment, the composition also includes particles of a third density; particles of a third and fourth density; particles of a third, fourth, and fifth density; or particles of a third, fourth, fifth, and sixth density, and so on. For example, in one embodiment, the particle composition has particles of two densities; in another, three densities; in yet another, four densities; in still another, five densities; and in yet another, six densities. According to one embodiment of the invention, the composition has particles of more than six different densities. In yet another embodiment, a particle may be a composite of more than one material, for example, a combination of different ECM types, each ECM type having a different density.

In one embodiment of the invention, the composition has particles of a first density and particles of a second different density where the particles of the second density are more dense than the particles of the first density. In a further embodiment, the particles of the second density are at least about 150% of the density of the particles of the first density (i.e., 1.5 times more dense). This magnitude of difference in density is necessary such that the difference between the rate of bioresorption of the particles of the first density and the rate of bioresorption of the particles of the second density is large enough to allow the tissue being treated to be repaired before the composition is fully resorbed. Particles of a second density having a density less than about 150% of the first density do not have a bioresorption profile significantly different from the bioresorption profile of particles of the first density to allow the tissue site to be repaired before the composition is completely resorbed.

In a further embodiment, the composition further includes particles of a third density. Particles of the third density are more dense than particles of the second density; the particles of the second density are more dense than particles of the first density. In a particular embodiment, the particles of the third density are at least about 150% of the density of the particles of the second density and the particles of the second density are at least about 150% of the density of the particles of the first density (i.e., 1.5 times more dense). Again, this magnitude of difference in density is necessary such that the difference between the rates of bioresorption between the particles of the first density, the second density, and the third density is large enough to allow the tissue being treated to be repaired before the composition is fully resorbed.

in a further embodiment, the particles of a second density that are more dense than particles of a first density have a resorption rate of about 1 time, about 2 times, about 3 times, about 4 times, about 5 times, about 6 times, about 7 times, about 8 times, about 9 times, or about 10 times, for example, the rate of resorption of the particles of a first, less density.

In a further embodiment, the particles of a second density are at least about 2 times, 2.5 times, 3 times, 3.5 times, 4 times, 4.5 times, or 5 times more dense than the density of the particles of a first density. In another embodiment, the particles of a third density are at least about 2 times, 2.5 times, 3 times, 3.5 times, 4 times, 4.5 times, or 5 times more dense than the particles of a second density.

Preferably, the second density particles are at least about 150-500% of the density of the lower first density particles, more preferably about 200-400% of the density of the lower first density particles, and most preferably about 200-300% of the density of the lower first density particles.

The particles according to one embodiment of the invention are extracellular matrix particles (ECM). According to the invention, ECM from which the particles of differing density are made may be derived from native tissues including, but not limited to submucosa, dermis, epithelial basement membrane, aponeurosis, tendon, ligament, smooth and skeletal muscle, and treatment site-specific ECM. The native tissue source may be porcine, bovine, or ovine, for example. The native tissue source may be alogenic, autogenic, or xenogenic to the patient. For example, if the patient is a human, the native tissue source is from another human (alogenic) or from the patient (autogenic). Alternatively, if the patient is a human, the native tissue is from a non-human species (xenogenic).

ECM particles according to the invention have densities ranging from about 150 mg/cm$^3$ to about 1800 mg/cm$^3$, more preferably from about 150 mg/cm$^3$ to about 1200 mg/cm$^3$, and most preferably from about 150 mg/cm$^3$ to about 600 mg/cm$^3$.

in another embodiment of the invention, particles of the invention are composed of, for example, collagen, i.e., type I, II, III and/or IV collagen; a bioresorbable polymer such as 30 poly (L) lactic acid, poly (D) lactic acid, polyglycolic acid, polydioxanone, or tyrosinepolycarbonate, and/or hyaluronic acid. Collagen particles according to the invention have densities ranging from about 150 mg/cm$^3$ to about 1800 mg/cm$^3$, more preferably from about 150 mg/cm$^3$ to about 1200 mg/cm$^3$, and most preferably from about 150 mg/cm$^3$ to about 600 mg/cm$^3$. Bioresorbable polymer particles according to the invention have densities ranging from about 150 mg/cm$^3$ to about 1800 mg/cm$^3$, more preferably from about 150 mg/cm³ to about 1200 mg/cm³, and most preferably from about 150 mg/cm³ to about 600 mg/cm³.

According to one embodiment of the invention, bioactive materials such as growth factors, DNA, or other proteins are added to particles of bioresorbable polymers for release as the polymers are resorbed in the patient. In another embodiment, bioactive materials such as growth factors, DNA, or other proteins are added to ECM compositions of the invention for release as the ECM is resorbed in the patient.

In one embodiment according to the invention, all particles of the first density are made from a first starting material and all particles of the second density are made from the same first starting material. For example, in one embodiment, all particles of the first density are made of an ECM material having a first density and all particles of the second density are particles of the same ECM material, but manipulated to have a second, different density. For example, the particles of a first density and the particles of the second density are each UBM particles. In another embodiment, all particles of the first density are a bioresorbable polymer and all particles of the second density are the same bioresorbable polymer. For example, the particles of the first density and the particles of the second density are poly (L) lactic acid.

In another embodiment, all particles of the first density are made from a first material and all particles of the second density are made from a second material. For example, all particles of the first density are made from a first ECM material and all particles of the second density are made from a second ECM material. For example, in one embodiment, the particles of the first density are made of UBM while particles of the second density are made from SIS. In another embodiment, all particles of the first density are made from an ECM material while all particles of the second density are made from a bioresorbable polymer. In another embodiment, the first material is UBM, while the second material is aponeurosis. In another embodiment, the first material is UBM, while the second material is liver basement membrane (LBM). In yet another embodiment, the first material is UBM, while the second material is hyaluronic acid. In an even further embodiment, the first material is UBM, while the second material is polylactic co-glycolic acid) (PLGA).

Particles according to one embodiment of the invention range from about 0.1 μM to about 2000 μM. More preferably, the particles range in size from about 1 μM-about 2000 μM, even more preferably from about 1 μM-about 1000 μM, and most preferably from about 50 μM-about 750 μM in width, for example, diameter.

According to one embodiment of the invention, the mixture of differing density particles is maintained in a powder form, while in another embodiment, the mixture of particles is maintained in a gel or liquid carrier for injection at a tissue site in a patient. Examples of suitable carriers include but are not limited to hyaluronic acid, gelatin, lecithin, collagen gel, and saline.

In a further embodiment, particles according to the invention contain growth factors and/or other biologically active molecules. For example, particles such as ECM may naturally contain biologically active molecules that are released at the site of implantation as the ECM is bioresorbed by the patient. Alternatively, biologically active molecules may be added to the composition of parades to be delivered to the site of implantation with the particles. In yet another embodiment, particles according to the invention are coated with biologically active molecules. In yet another embodiment, particles of bioresorbable polymers are synthesized and formed into particles in the presence of biologically active molecules so that the biologically active molecules are contained within the bioresorbable polymer particle.

Examples of biologically active molecules include, but are not limited to epidermal growth factor, TGF-alpha, TGF-beta, fibroblast growth factor, platelet derived growth factor, vascular endothelial growth factor, insulin-like growth factor, keratinocyte growth factor, and bone morphogenic protein to name a few, as well as pharmaceutical agents, and DNA vectors.

According to the invention, particles release biologically active molecules in a time dependent fashion. For example, given that lower density particles are bioresorbed by patient tissue at a more rapid rate than higher density particles, biologically active molecules, such as growth factors, are released from lower density particles relatively quickly after implantation as compared to their release from higher density particles. Higher density particles bioresorb more slowly and therefore release biologically active molecules at the tissue site over a longer period of time than the lower density particles, thereby exposing the tissue site to particular biologically active molecules for a longer period of time than if only lower density particles are present.

According to another aspect, the invention relates to methods of making mixtures of particles where a first type of particle has a first density and a second type of particle has a second density.

Figure 3:
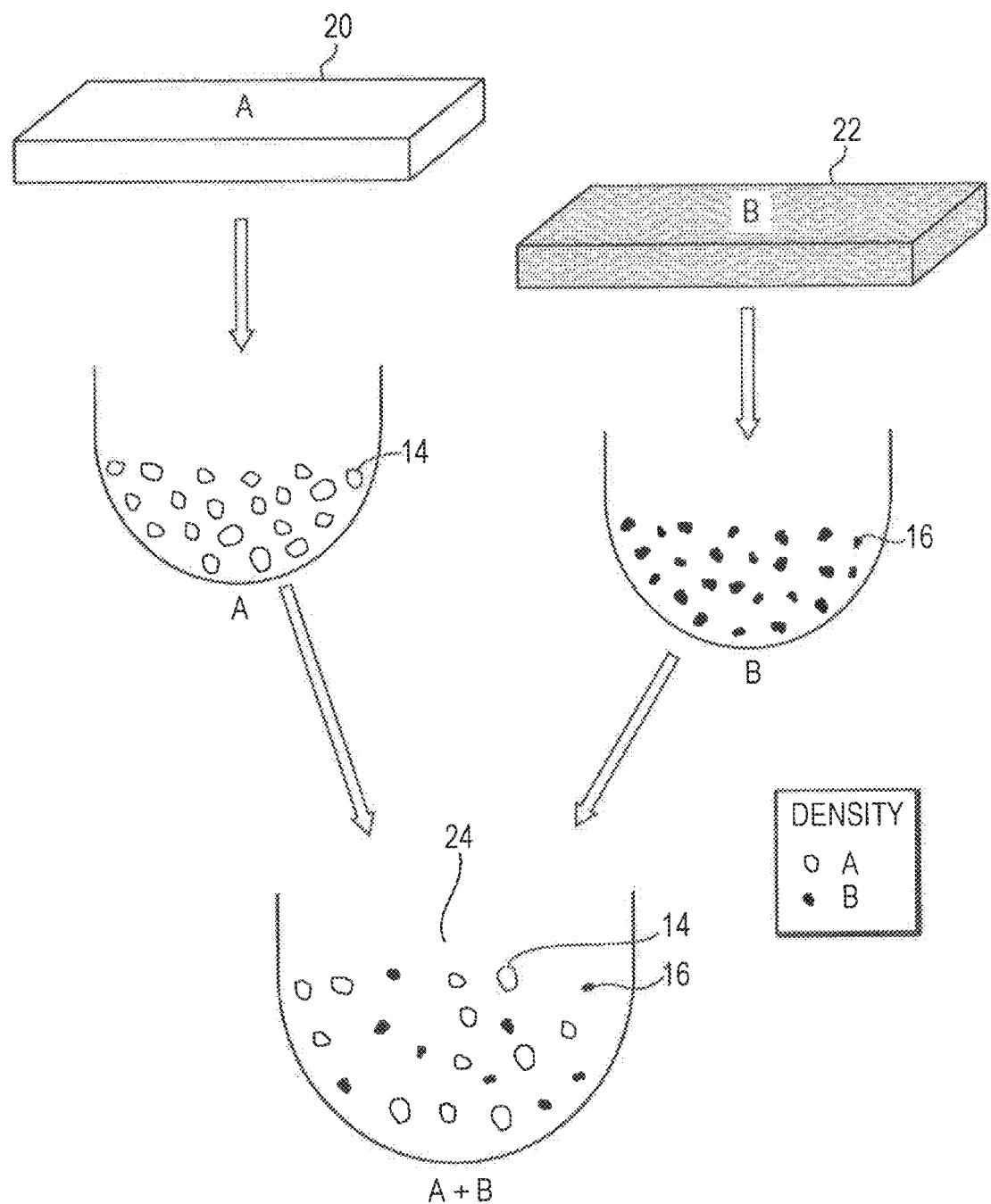
FIG. 3 depicts an exemplary composition of ECM particles according to one embodiment of the invention where the particles are of two different densities and the stages of an exemplary method of making the composition according to one embodiment of the invention. Two sheets of ECM are shown, one having density A and the other having density B. The sheets are comminuted and a portion of A particles and B particles are mixed together.

According to one embodiment of the method of making mixtures of particles of the invention, sheets of ECM are comminuted to create a mixture of particles of differing density. For example, as shown in FIG. 3, a mixture 24 of A particles 14 and B particles 16 where A particles 14 are less dense than B particles 16 is made from two ECM sheets 20, 22 of differing densities. A Sheet 20 is comminuted to form A particles by chopping, cutting, pulverizing, milling, or grinding A Sheet 20 with a suitable device that forms particles such as a blender, a hammer mill, a knife mill, a centrifugal mill, a die and press system, or a roller crusher, for example. B Sheet 22 is comminuted to form B particles 16 by chopping, cutting, crushing, pulverizing, milling, mincing, or grinding B Sheet 22 with a suitable device to form particles 16, A particles 14 and B particles 16 have size ranges and density ranges as described above.

To form the mixture, a predetermined number of A particles 14 is then measured and 15 mixed with a predetermined number of B particles 16 to form a composite mixture 24 of A particles 14 and B particles 16, where the concentration of A particles 14 to B particles 16 is predetermined based on a particular desired resorption profile of the mixture at a tissue site in a patient. For example, for a tissue site that takes a long time to repair, such as a joint, fewer less dense A particles 14 are selected compared to the number of higher density B particles 16 in order to provide a prolonged resorption of EGM at the tissue site. A particles 14 may be selected at a ratio of (A:B) 1:1, 1:2, 1:3, 1:4: 2:3, 3:4, 2:1, 3:1, 3:2, 4:3, or 4:1 B particles 16, for example, depending on the particular tissue site to be treated and the desired resorption profile of the particles for treating that tissue site.

According to a further embodiment of the invention, a mixture of particles includes three types of particles, each type of a differing density. For example, the mixture includes low density particles, intermediate density particles, and higher density particles. For example, according to the invention, a sheet of a third density (C) is comminuted to form particles of a third density C, higher than the density of particles formed from A sheet 20 and B sheet 22. A predetermined number of particles of the third density are measured out and added to the mixture of A particles 14 and B particles 16. Particles of a third density may be selected at a ratio of (A:B:C) 1:1:1, 1:1:2, 1:1:3, 1:1:4, 1:2:1, 1:2:2, 1:2:3, 1:2:4, 1:3:1, 1:3:2, 1:3.3, 1:3:4, 1:4:1, 1:4:2, 1:4:3, 1:4:4, 2:1:1, 2:1:2, 2:1:3, 2:1:4, 2:2:1, 2:2:3, 2:3:1, 2:3:2, 2:3:3, 2:3:4, 2:4:1, 2:4:3, 3:1:1, 3:1:2, 3:1:3, 3:1:4, 3:2:1, 3:2:2, 3:2:3, 3:2:4, 3:3:1, 3:3:2, 3:3:4, 3:4:1, 3:4:2, 3:4:3, or 3:4:4, for example, depending on the particular tissue site to be treated and the predetermined resorption profile of the particles for treating the tissue site.

For example, in one embodiment, a composition of the invention has two parts lower density particles to 1 part higher density particles (2:1) and is used for wound treatment, i.e., of the skin and skin adnexa. The higher concentration of lower density particles, when applied to a wound, provides a rapid influx of bioactive components to activate the restoration and repair process as the lower density particles are bioresorbed, followed by a longer term release of bioactive components over time at the implantation site as the higher density particles resorb slowly over time. Additionally, specific bioactive components may be added to the lower or higher density particles to tailor the release of bioactive components to the stage of restoration and repair at the tissue site.

in another embodiment, a composition of the invention has 1 part lower density particles to four parts higher density particles (1:4) or 1 part lowest density particles, 2 parts lower density particles, and 2 parts highest density particles, (1:2:2) and is used for tendon or ligament repair. Restoration and repair of tendons and ligaments takes longer than at body sites that are typically more vascular and more cellular. Accordingly, the 1:4 or 1:2:2 density profile composition provides a longer resorption profile of the composition for restoring or repairing tendons and ligaments as compared to traditional ECMs.

In yet another embodiment, a composition of the invention has 2 parts lower density particles to 3 parts higher density particles to (2:3) and is used for scar revision or plastic surgery applications to promote a rapid early tissue restoration response while also having prolonged bioactive component release at the site to help prevent hypertrophic scar formation over a longer time.

In yet another embodiment, a composition of the invention has one part lower density particles to 2 parts higher density particles (1:2) and is used for applications involving soft tissue augmentation. In a further embodiment, a composition of the invention has one part lower density particles to 3 parts higher density particles (1:3) and is used for ophthalmological applications.

According to the invention, sheets of ECM 20, 22 can be treated to alter their densities prior to being comminuted. The density of a sheet of ECM can be increased by mechanically compressing the material, dehydrating the material, vacuuming the material, cross-linking the material, or lyophilizing the material, for example. The density of a sheet of ECM can be decreased by hydration, expanding the pore structure under vacuum, mechanically expanding the material, or freezing the material in water, for example.

Figure 4:
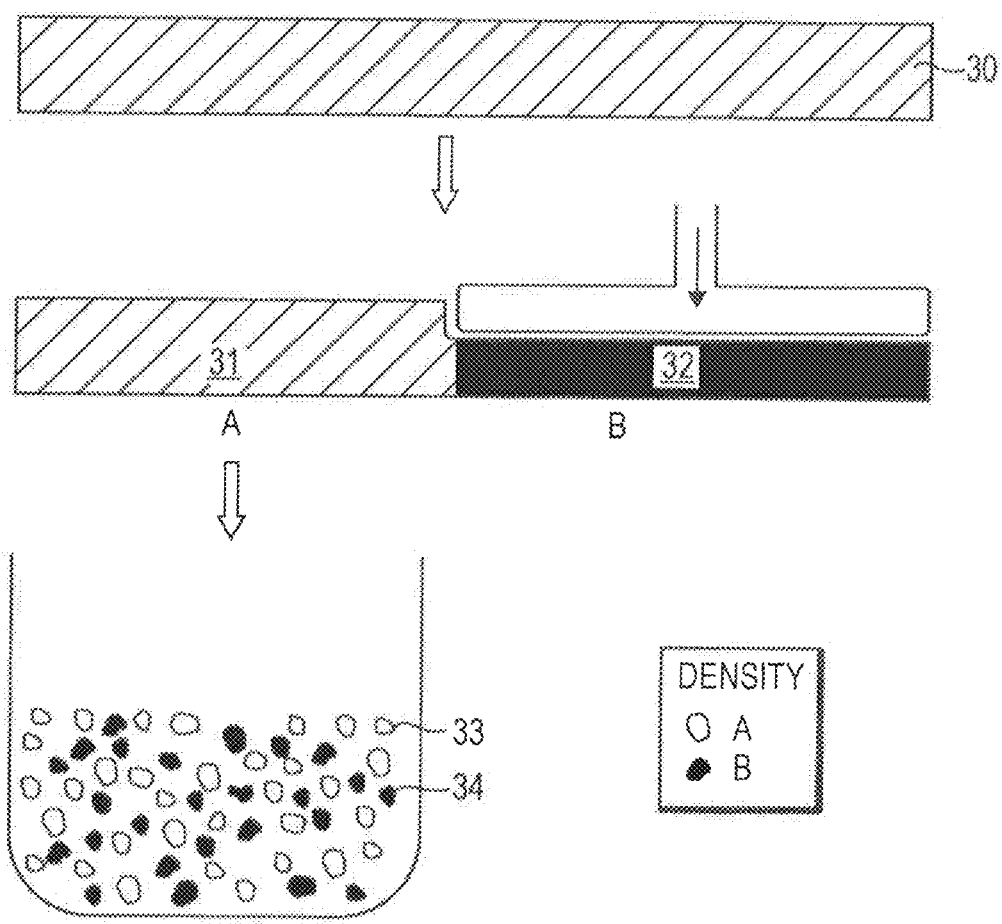
FIG. 4 depicts an exemplary composition of ECM particles according to one embodiment of the invention where the particles are of two different densities and the steps of an exemplary method of making the composition according to one embodiment of the invention. A sheet of ECM is treated so that a portion of the sheet has a density A and a second portion of the sheet has a density B. The sheet is then comminuted to make a composition of particles of two different densities.

In another embodiment of the method of making a mixture of particles having a first density A and particles having a second density B, particulate matter from a sheet of ECM having areas of density A and density B are removed from the sheet of ECM and mixed together. For example, as shown in FIG. 4, sheet 30 is partially compressed to form a sheet 30 having an area A 31 of a first lower density and area B 32 of a second higher density. The sheet 30 is then milled to produce particles 33 from area A 31 having a lower density A and particles 34 from area B 32 having a higher density B.

According to one embodiment of the invention, the portion of sheet 30 that is compressed relative to the portion that is not compressed or less compressed is determined based on the predetermined bioresorption profile for the particles at a given tissue site in a patient. Accordingly, for example, if a 1:1 ratio of A:B (low density:high density) particles is sought to achieve the desired bioresorption profile, one half of the sheet is compressed to the desired density prior to comminuting the sheet into a mixture of particles of A and B densities. In one embodiment, the size of sheet 30 is selected prior to compression of a portion of the sheet 30 and the whole sheet 30 is comminuted after compression. Alternatively, in another embodiment, a portion of the sheet 30 is compressed after which a portion of sheet 30 is cut away from the whole of sheet 30 with the cut-away portion being comminuted.

In a further embodiment, a portion of the sheet 30 is compressed to have a third density C. The sheet 30 is then milled to produce a mixture of particles having a density A, a density B, and the third density C. The third density may be higher than A or higher than A and B.

Figure 5:
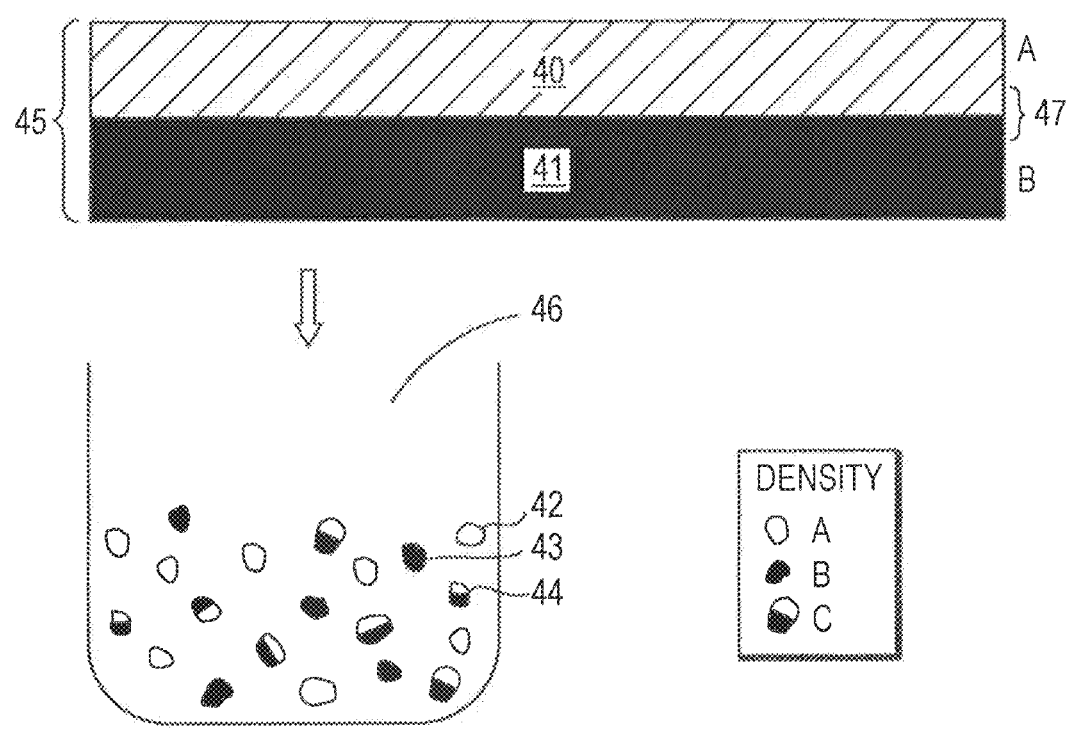
FIG. 5 depicts an exemplary composition of ECM particles according to one embodiment of the invention where the particles have a density A, B, or C and the steps of an exemplary method of making the composition according to one embodiment of the invention. A first sheet A of ECM having density A is adhered to a second sheet B of ECM having density B. The sheet is then comminuted to create a composition of particles having density A and particles having density B and composite particles of density C, the composite particles having components of both sheets A and B.

Another embodiment of the method of making a mixture of particles having differing densities is shown in FIG. 5. According to one embodiment, a sheet 40 of ECM of a first density A is joined with a sheet 41 of ECM of a second density B to form a composite sheet 45. The composite sheet 45 is then comminuted to create a mixture of particles 46 having different densities. For example, when composite sheet 45 is comminuted, the mixture includes A particles 42 of low density derived from sheet A, B particles 43 of a higher density derived from sheet B, and C particles 44 of an intermediate density formed from the interfacing area 47 of the A sheet 40 and the B sheet 41.

Figure 6:
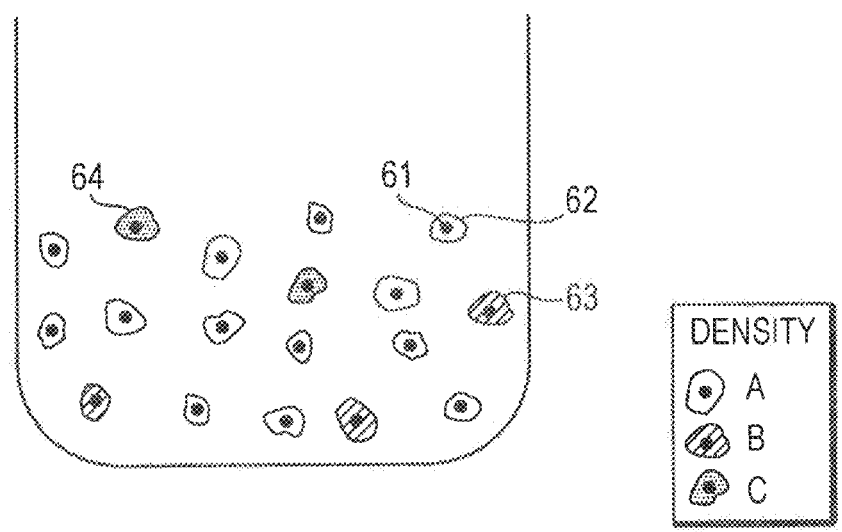
FIG. 6 depicts an exemplary composition of ECM particles according to one embodiment of the invention where the particles have a core particle of the same density, but are coated with different materials having different densities A, B, and C. Accordingly, the coated particles have differing densities A, B, and C.

A further embodiment of the method of making a mixture of particles having different densities is shown in FIG. 6. According to this embodiment, particles 65 have a core 61 and a coating 62. The core 61 has a density X and may be coated with any of a variety of coatings 63, 64, 66 having a variety of densities. For example, some particles 65 have cores 61 coated with a first material 66 having a first density to produce particles having a density A, while other particles 65 have cores 61 that are coated with a second material having a second density 63 to produce particles having a density B, while yet other particles 65 have cores 61 coated with a third material having a third density 64 to produce particles having a third density C. Coating the core 61 can be performed, for example, by precipitating the coating onto a particle from a solution, by a roll coater, or by a granulator. Materials for coatings may include, fir example, an ECM, a gel made from an ECM such as UBM gel or SIS gel, PLGA, hyaluronic acid, or collagen, for example. The core 61 of particles 65 may include, fbr example, ECMs as described herein.

Figure 7:
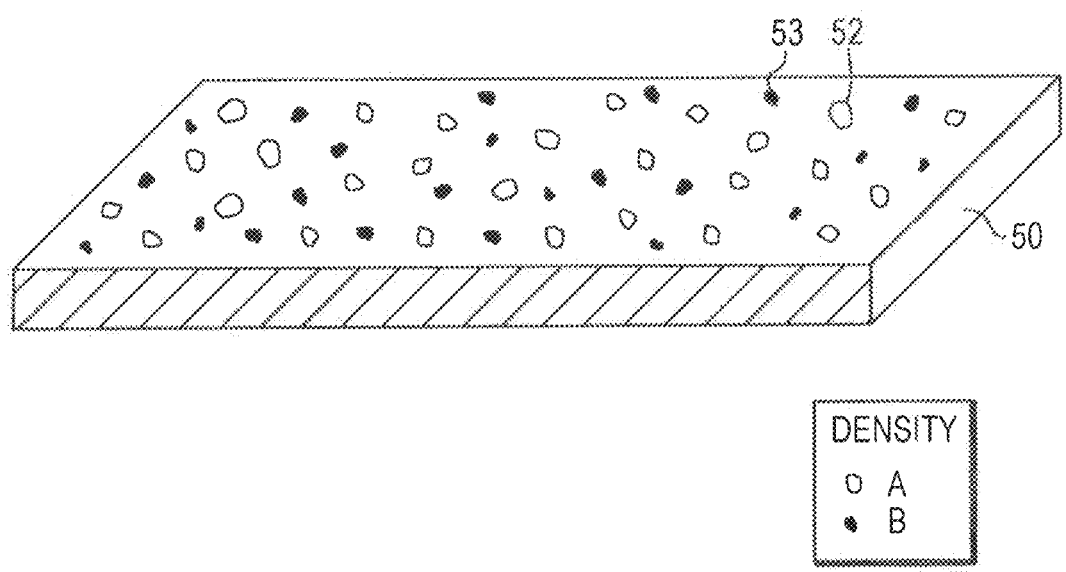
FIG. 7 depicts an exemplary ECM composition according to one embodiment of the invention where ECM particles having densities A, B, and C are adhered to the surface of a sheet 25 of ECM.

In another aspect of the invention, mixtures of comminuted particles of differing density are coated on devices such as synthetic or natural wound repair matrices for implantation into a patient. For example, as shown in FIG. 7, a mixture of A lower density particles 52 and B higher density particles 53 is applied to a sheet 50 of ECM. The particles 52, 53 are adhered to the sheet by compression or use of an adhesive, for example. Accordingly, when the sheet 50 is implanted at a tissue site in a patient, the particles 52, 53 provide more surface area to contact with the tissue site in the patient. The A particles 52 and B particles 53 are more dense in one embodiment than the ECM sheet 50 so that after the sheet 50 has been fully resorbed, the tissue continues to repair in the presence of particles 52 and 53. The remaining particles 52, 53 allow the tissue to repair before the particles 52, 53 of the composition are completely resorbed.

In a further embodiment, mixtures of comminuted particles of differing density coated on a device such as a synthetic or natural wound repair matrix is implanted in a patient for use as an adhesion barrier. For example, as shown in FIG. 7, a matrix in sheet form 50, for example, is coated on one side with particles 52, 53 of differing density according to the invention and is implanted in a patient. Any adhesions forming at the implant site adhere to the particulate side of the matrix and as the particles 52, 53 are resorbed, the adhesions no longer remain attached to the matrix, but to the particles and the adhesions are subsequently resorbed. In an alternative embodiment, particles of differing density according to the invention are sandwiched between a first matrix sheet of a first heavier density and a second matrix sheet of a lighter density to form an implant. The implant is implanted at a site in the patient with the more dense matrix sheet implanted against the tissue requiring repair and the less dense sheet facing outward into the body of the patient. As adhesions form on the outward facing less dense sheet, the less dense sheet is resorbed allowing any adhesions to become unattached from the more dense portion of the implant, the adhesions then being subsequently resorbed by the patient along with the less dense sheet of matrix.

In one embodiment, the mixture of particles 52, 53 is adhered to one surface of the sheet 50, while in another embodiment the mixture of particles 52, 53 is adhered to all surfaces of the sheet 50. For example, the sheet 50 bioresorbs in the patient within 60 days, the lower density A particles bioresorb in 7 days, and the higher density B particles bioresorb in the patient within 30 days.

In a further embodiment, a mixture of comminuted particles according to the invention is coated on a surgical medical device prior to the devices' implantation at a tissue site in a patient. For example, a mixture of lower density A particles and higher density B particles are coated on a medical implant such as, but not limited to, a stent, a cardiac occluder, suture material, or a mesh. The particles are adhered to the device by, for example, a chemical bond, a peptide linker, a bioresorbable adhesive, such as cyanoacrylate or fibrin glue, or by mechanical means such as lyophilization of the particles on the device or compressing the particles onto the device. Once the device is implanted at the tissue site in the patient, the lower density A particles bioresorb quickly providing an initial restoration response at the tissue site in the patient, while the higher density B particles are not fully bioresorbed until the tissue site is completely repaired. For example, the lower density A particles are bioresorbed by the patient within, for example, 7 days, while the higher density B particles are bioresorbed by the patient within, for example, 30 days.

Figure 8A:
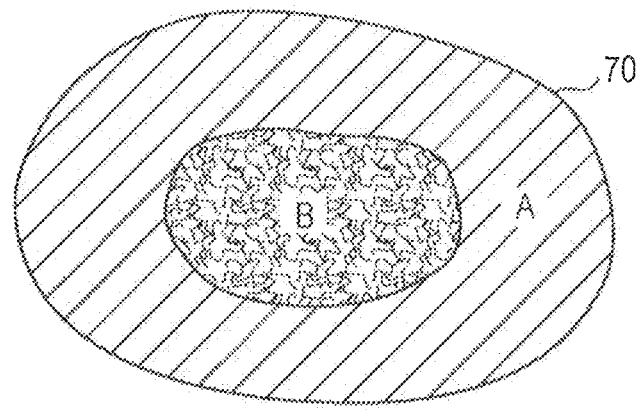
FIG. 8A depicts an exemplary ECM composition according to one embodiment of the invention where ECM particles of a higher density B are compressed together to form a core of particles of density B coated with particles of lower density A or layered with a layer of particles of density A to form a construct in the shape of a mammalian body part, here exemplified as a kidney.
Figure 8B:
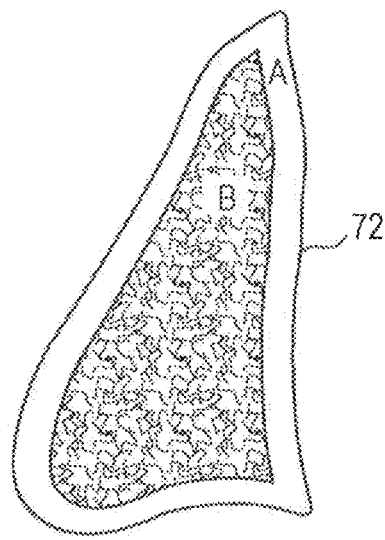
FIG. 8B depicts an exemplary ECM composition according to one embodiment of the invention where ECM particles of a higher density B are compressed together to form a core of particles of density B coated with particles of lower density A or layered with a layer of particles of density A to form a construct in the shape of a mammalian body part, here exemplified as a human nose.

In another aspect, the invention includes aggregates of particles of differing density which form an implant with portions of differing densities for implantation at a tissue site in a patient. According to the invention, as shown in FIGS. 8A and 8B, high density particles B are compressed to form a shape replicating a body part or portion of a body part in a mammal, for example, a human, and form the core 71 *a, b* of an implant 70, 72. Lower density particles A are then compressed or coated around the 71 *a, b* core of B particles to form the peripheral layer of the implant 70, 72. As shown in FIG. 8A, the A and B particles form an ovoid shape implant 70 to be used in replacement or repair, for example, of a kidney or liver. As shown in FIG. 5B, the peripheral A and core B particles form roughly a triangular shape implant 72 to be used in replacement or repair, for example, of a nose.

Figure 9:
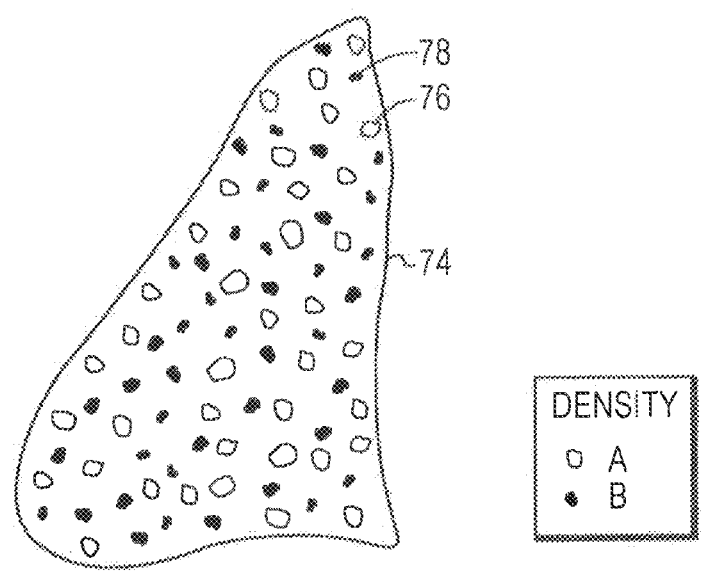
FIG. 9 depicts an exemplary ECM composition according to one embodiment of the invention where a mixture of ECM particles of a higher density B and of a lower density A are compressed together to form a three-dimensional construct in the shape of a mammalian body part, here exemplified as a human nose.
Figure 10:
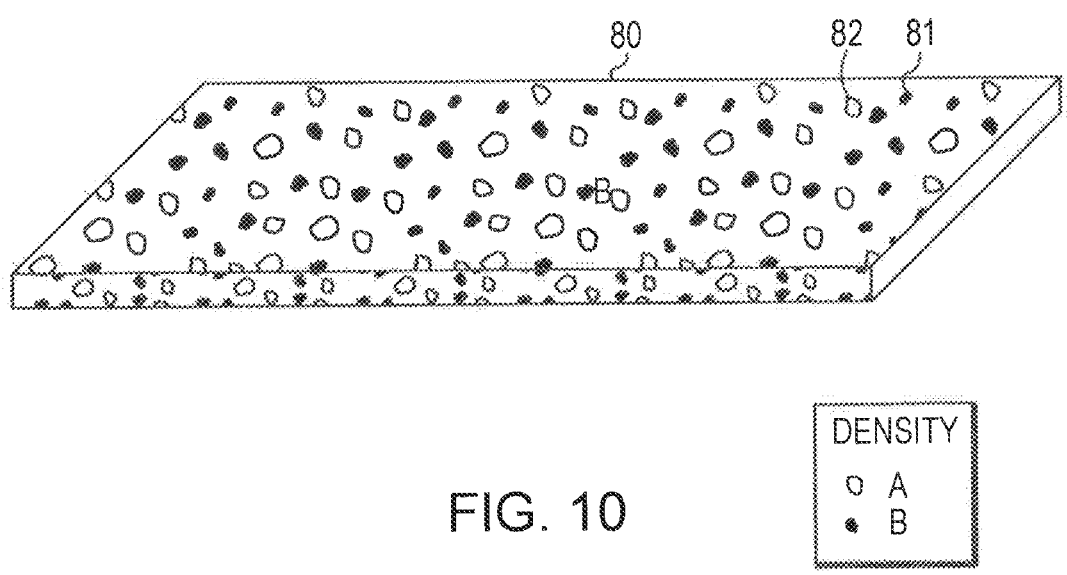
FIG. 10 depicts an exemplary ECM composition according to one embodiment of the invention where a mixture of ECM particles of a higher density B and of a lower density A are compressed together to form a sheet.

The implant 70, 72 is implanted into a patient at a site requiring restoration or repair, for example. Upon implantation, the peripheral A particles having a lower density provide an immediate repair and restoration response at the tissue site in the patient. After the peripheral A particles rapidly bioresorb, the higher density core 71 *a, b* B particles continue to provide a repair and restoration response at the tissue site in the patient over a longer period of time than the peripheral A particles alone. The core 71 *a, b* B particles are typically not fully resorbed by the patient until the tissue site is repaired. For example, the peripheral A particles of lower density are bioresorbed by the patient within, for example, 14 days, while the core B particles of higher density are bioresorbed by the patient within, for example, 60 days.

in a further embodiment, as shown in FIG. 9, an implant 74 can be formed by compressing a mixture of lower density A particles 76 with higher density B particles 78. The lower density particles 76 resorb at a faster rate which create channels in the implant and provide space for body tissue to grow into the implant, while the higher density particles resorb more slowly, providing structural support for the construct as tissue restoration and repair occurs and releasing bioactive components over time as the higher density particles resorb. The implant 74 can be compressed into any number of three dimensional shapes such as a kidney, spleen, nose, ear, liver, bone, or other body organ.

In another embodiment of the invention, a three dimensional construct of compressed particles of varying density is made to mimic natural biologic tissue densities. For example, in one embodiment, a construct is made with denser particulate matter on one side, of a sheet for example, and more dense particulate matter is placed on the other side. Such a construct can be used at a bone-cartilage interface where the more dense portion is inserted into the bone defect while the less dense portion is positioned in the cartilage defect. The slower resorbing, higher density particulate remodels according to the slower rate of bone generation resulting in more dense tissue restoration consistent with bone, while the less dense portion remodels more quickly and creates a less dense tissue restoration consistent with cartilage. The invention also contemplates three dimensional constructs of compressed particulate having different density regions that are designed, for example, to mimic the native density variations of a spinal disc or the muscle-tendon interface.

in a further embodiment, as shown in NG. 10, a sheet 80 is formed by compressing a mixture of lower density A particles 81 with higher density B particles 82. The sheet 80 can be formed, for example, by hydrating the particles and compressing the particles together by application of a mechanical force or vacuum to form a cake or wafer-like construct. The sheet 80 can be used to treat topical wounds, for example, of the skin, but can also be used to treat other areas of the body such as a hernia, intestine, bowel, blood vessels, the heart, or any other organ, by cutting the sheet to size and/or bending or wrapping the sheet to fit the implant location. The sheet 80, with its differing density particles, will break down on implantation as a result of bioresorption of the lower density particles, providing greater surface area for tissue restoration and repair at the site of implantation. The sheet form 82 has the benefit of being easy to apply to the implant site, but also has the ability to provide a prolonged restoration response at the implant site as the particles 81, 82 are resorbed at different rates, in contrast to sheets made of only one density of material.

Figure 11:
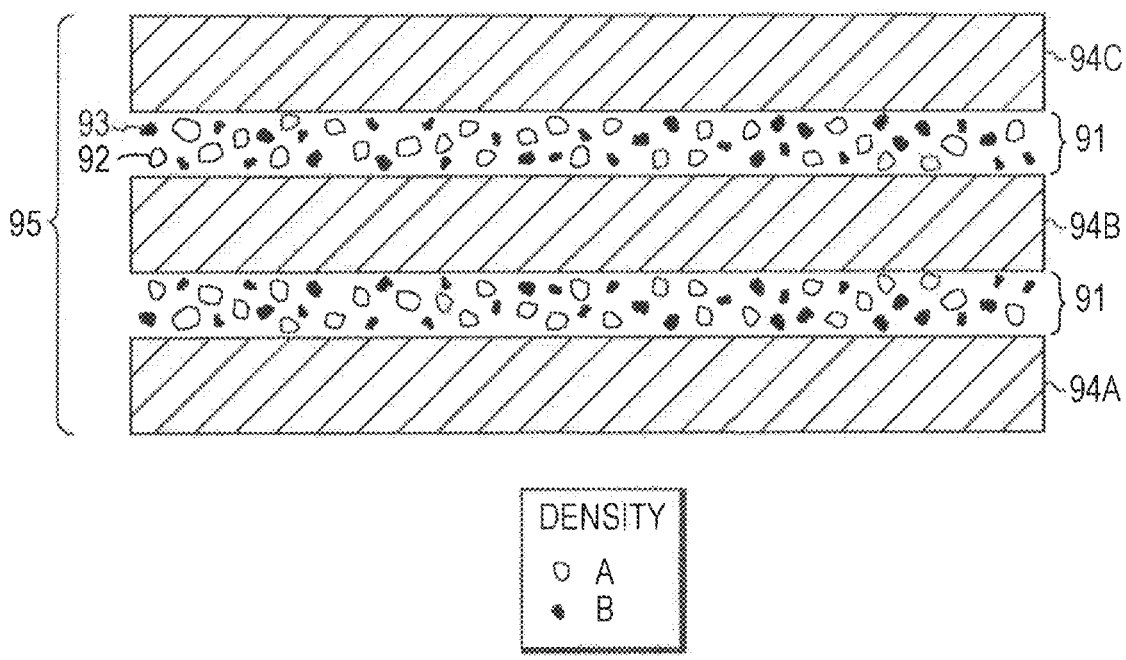
FIG. 11 depicts an exemplary multi-laminate ECM composition according to one embodiment of the invention where a mixture of ECM particles of a higher density B and a lower density A are sandwiched between sheets of ECM.

In a further embodiment, as shown in FIG. 11, mixtures of particles 91 of differing densities, i.e., A particles of a first density 92 and B particles of a second density 93, are sandwiched between sheets 94 of an ECM. For example, a powder form mixture of particles of a first density A 92 and a second density B 93 is sandwiched between sheets 94 of UBM or SIS to form a multi-laminate construct 95 of loose particles 91 and sheets 94. Any number of alternating layers of sheets 94 and the mixture 91 of particles 92, 93 can be constructed according to the invention. For example, in one embodiment, a first sheet 94A is covered with the particle mixture 91; the particle mixture 91 is covered with a second sheet 94B; the second sheet 94B is covered with the particle mixture 91; and a third sheet 94C applied to form a sheet-particle-sheet-particle-sheet multi-laminate construct 95. The sheets of multi-laminate construct 95, when implanted at a site in a patient, provide a microarchitecture for tissue restoration at the site while the particles 92, 93 breaking down at varying rates provide a continuous supply of bioactive factors to assist in restoration at the implant site.

In a further embodiment, particles of a lower density A and particles of a higher density B can be combined with a bone substitute material such as beta-tricalcium phosphate (βTCP), hydroxyapatite, sintered bovine bone, sintered porcine bone, demineralized allograft bone, or mineralized allograft bone, for example. In an alternative embodiment, the bone particles and the differing density ECM particles of the invention can be mixed together without an adhesive, binder, or any other additive. The particles are coated on and/or injected into the bone substitute material. When the bone substitute material is implanted at the tissue site in the patient, the bone substitute material provides a rigid form to stabilize the defect while the lower density particles promote rapid tissue repair at the site. Over time, the higher density particles sustain tissue repair at the site of implantation as they are bioresorbed at a slower rate than the lower density particles. The higher density particles are typically not fully bioresorbed until the tissue site is repaired.

According to another embodiment of the invention, a mixture of particles having particles of a lower density A and particles of a higher density B are provided in powder form, A powder has particles of 1-1000 µm. The powder can be sprinkled topically on a tissue site in a patient, for example, a cut, scrape, incision, or puncture of the skin, or while a tissue site is exposed during surgery, the powder form can be sprinkled at the tissue site. In another embodiment, the differing density particles are administered via inhalation, for example, through use of an inhaler such as those used to administered asthma treatments.

In an alternative embodiment, a mixture of particles of a lower density A and particles of a higher density B are maintained in a liquid, gel or paste medium. The liquid or gel is injected via a syringe at a tissue site in a patient. Alternatively, the liquid or gel is maintained within a tube and is squeezed out of the tube and applied to the tissue site. In a further embodiment, the powder, liquid, gel, or paste composition includes particles of a third density.

In another aspect, the invention encompasses methods for modulating the rate of tissue restoration at a tissue site in a patient in need of repair or restoration. The method requires administering to a site in a patient a mixture that includes at least two types of particles, each type having a different density, one type of particle being more dense than the other type of particle. The differing density particles are selected to form the mixture based on their respective bioresorption profiles, i.e., the higher density particles are selected because they take longer to be resorbed at the tissue site than the particles of a louver density and the lower density particles are selected because they will be resorbed quickly at the tissue site. According to the invention, a physician particularly selects the mixture to have particles with particular rates of bioresorption tailored for the particular tissue site to be repaired or restored. The mixture is administered to the patient topically, via injection to the tissue site, or it may be delivered to the tissue site surgically, for example.

Tissue sites treatable with compositions according to the invention include, but are not limited to head and neck structures, joints including synovium, joint capsule, labrum, intraarticular ligaments and cartilage, intervertebral discs, pelvic floor, tendon, bone, ligament, kidney, spleen, liver, muscle tissue, urinary bladder, ureter, uterus, intestine, pancreas, blood vessel, skin and skin adnexa, heart including intracardiac structures, nose, ear, breast, or a body cavity.

EXAMPLES

1. Tissue Restoration of a Chronic Skin Ulcer

A mixture of ECM particles is made by taking 60 mg of particles of UBM of size 50-1000 µm and having a density of approximately 0.05 g/cm$^3$ and 20 mg of particles of UBM of size 50-500 µm and having a density of approximately 0.25 g/cm$^3$, for a 3:1 ratio of particles based on weight. The mixture is applied topically to a chronic skin ulcer. Within 10 days, the 0.05 g/cm$^3$ particles are resorbed and tissue restoration is observed at the wound site. Within 30 days, the 0.25 g/cm$^3$ particles are resorbed and tissue at the wound site is fully restored.

2. Tissue Restoration of a Kidney

A mixture of ECM particles is prepared for implantation in a kidney at a site from which a tumor has been excised. A mixture of ECM particles is made by taking 200 mg of particles of UBM of size 500-1000 µm and having a density of approximately 0.10 g/cm$^3$ and 1000 mg of particles of UBM of size 50-500 µm and having a density of approximately 0.35 g/cm$^3$, for a 1:5 ratio of particles based on weight. The mixture is surgically implanted in the patient via a syringe. Within 20 days, the 0.1.0 g/cm$^3$ particles have resorbed and tissue restoration is observed at the wound site via magnetic resonance imaging. Within 60 days, the 0.35 g/cm$^3$ particles are resorbed and tissue at the wound site is fully restored as viewed via magnetic resonance imaging.

What is claimed is:

1. A method of modulating the rate of tissue repair at an anatomical site in a patient in need of repair or restoration, the method comprising:
   administering to a patient at the anatomical site an implant comprising at least one extracellular matrix material comprising,
   a first plurality of bioresorbable particles comprising a native extracellular matrix comprising an epithelial basement membrane and tunica propria and a plurality of other naturally associated native extracellular matrix components and having a first density, and
   a second plurality of bioresorbable particles comprising an extracellular matrix having a second density that is at least 150% of the first density, wherein the second plurality of bioresorbable particles are resorbed by the patient's tissue at a slower rate than the absorption of the first plurality of bioresorbable particles; and administering said implant at the anatomical site of the mammalian patient.

2. The method of claim 1, further comprising the steps of:
   (a) determining an optimal rate of absorption of said second plurality of bioresorbable particles for the repair or the restoration of the anatomical site in the mammalian patient;
   (b) selecting the second density of said second plurality of bioresorbable particles for said optimal rate of absorption determined in step (a).

3. The method of claim 1, wherein the first plurality of bioresorbable particles and the second plurality of bioresorbable particles of said implant are delivered to the anatomical site in the mammalian patient in powder form.

4. The method of claim 1, wherein the first plurality of bioresorbable particles and the second plurality bioresorbable particles of said implant are delivered to the anatomical site in the mammalian patient in a liquid or gel medium.

5. The method of claim 1, wherein the first plurality of bioresorbable particles and the second plurality bioresorbable particles of said implant are injected at the anatomical site in the mammalian patient.

6. The method of claim 1, wherein at least one of the first bioresorbable particles and the second plurality of bioresorbable particles contain one or more pharmaceutical agents.

7. The method of claim 1, wherein the implant comprises a third plurality of bioresorbable particles comprising a third density.

8. The method of claim 1, wherein the implant is administered to the patient via coating the first and the second plurality of bioresorbable particles on a medical device prior to implantation of the medical device at the anatomical site in the mammalian patient.

9. The method of claim 1, wherein the first and the second plurality of bioresorbable particles are administered topically to the anatomical site.

10. The method of claim 1, wherein the first plurality of bioresorbable particles and the second plurality of bioresorbable particles of said implant are administered to the mammalian patient as a component of a bone substitute material.

11. The method of claim 1, wherein the anatomical site in need of repair or restoration is selected from the group consisting of a tendon, a ligament, a bone, a kidney, a liver, a spleen, a lymph node, a bladder, a ureter, a uterus, a blood vessel, the skin, the breast, the bladder, the heart, and a body cavity.

12. The method of claim 1, wherein the patient is a human.

13. The method of claim 1 wherein the extracellular matrix material of said second plurality of particles comprises urinary basement membrane (UBM).

14. The method of claim 1 wherein the extracellular matrix material of said first and second plurality of particles comprises UBM.

15. The method of claim 1 wherein said second plurality of particles is 150-500% the density of said first plurality of particles.

16. The method of claim 1 further comprising forming said implant by providing a predetermined quantity of said first plurality of bioresorbable particles and a predetermined quantity of said second plurality of bioresorbable particles and mixing together said first predetermined quantity of bioresorhable particles with said predetermined quantity of said second plurality of bioresorbable particles.

17. The method of claim 16 wherein said second plurality of particles is 150-500% the density of said first plurality of particles.

* * * * *